US009562265B2

(12) United States Patent
Rohozinski (10) Patent No.: US 9,562,265 B2
(45) Date of Patent: Feb. 7, 2017

(54) PRIMERS AND METHODS FOR DETERMINING RHD ZYGOSITY (71) Applicant: Wake Forest University Health Sciences, Winston-Salem, NC (US)

(72) Inventor: Jan Rohozinski, Winston-Salem, NC (US)

(73) Assignee: Wake Forest University Health Sciences, Winston-Salem, NC (US)

(*) Notice: Subject to any disclaimer, the term of this patent is extended or adjusted under 35 U.S.C. 154(b) by 154 days.

(21) Appl. No.: 14/463,723

(22) Filed: Aug. 20, 2014

(65) Prior Publication Data

US 2014/0356878 A1  Dec. 4, 2014

Related U.S. Application Data (62) Division of application No. 12/887,675, filed on Sep. 22, 2010, now abandoned.

(60) Provisional application No. 61/244,711, filed on Sep. 22, 2009.

(51) Int. Cl.
C12Q 1/68 (2006.01)
C12P 19/34 (2006.01)

(52) U.S. Cl.
CPC ............. C12Q 1/686 (2013.01); C12Q 1/6881 (2013.01); C12Q 2600/156 (2013.01)

(58) Field of Classification Search
None
See application file for complete search history.

(56) References Cited

U.S. PATENT DOCUMENTS

| 4,521,509 | A | 6/1985 | Benkovic et al. |
| 4,683,195 | A | 7/1987 | Mullis et al. |
| 4,683,202 | A | 7/1987 | Mullis |
| 4,800,159 | A | 1/1989 | Mullis et al. |
| 4,889,818 | A | 12/1989 | Gelfand et al. |
| 4,965,188 | A | 10/1990 | Mullis et al. |
| 5,023,171 | A | 6/1991 | Ho et al. |
| 5,066,584 | A | 11/1991 | Gyllensten et al. |
| 5,075,216 | A | 12/1991 | Innis et al. |
| 5,075,217 | A | 12/1991 | Weber |
| 5,079,352 | A | 1/1992 | Gelfand et al. |
| 5,091,310 | A | 2/1992 | Innis |
| 5,104,792 | A | 4/1992 | Silver et al. |
| 5,364,759 | A | 11/1994 | Caskey et al. |
| 5,432,054 | A | 7/1995 | Saunders et al. |
| 5,538,848 | A | 7/1996 | Livak et al. |
| 5,723,293 | A | 3/1998 | Huang |
| 5,856,093 | A | 1/1999 | Brenner |
| 6,258,540 | B1 | 7/2001 | Lo et al. |
| 7,208,274 | B2 | 4/2007 | Dhallan |
| 7,252,949 | B2 | 8/2007 | Flegel et al. |
| 7,449,295 | B2 | 11/2008 | Hashmi et al. |
| 9,034,573 | B1 * | 5/2015 | Flegel .................. C07K 14/705 435/6.17 |
| 2002/0045176 | A1 | 4/2002 | Lo et al. |

FOREIGN PATENT DOCUMENTS

| EP | 1 780 217 A1 | 5/2007 |
| WO | WO 2006/032897 A2 | 3/2006 |
| WO | WO 2008/098142 A2 | 8/2008 |

OTHER PUBLICATIONS

Wagner FF et al. Molecular basis of weak D phenotypes. Blood. Jan. 1, 1999; 93(1): 385-393.
Wagner FF et al. Weak D alleles express distinct phenotypes. Blood. Apr. 15, 2000; 95(8): 2699-2708.
Wagner FF and Flegel WA. RHD gene deletion occurred in the Rhesus box. Blood. Jun. 15, 2000; 95(12): 3662-3668.
Chiu RWK et al. Determination of RhD zygosity: comparison of a double amplification refractory mutation system approach and a multiplex real-time quantitative PCR approach. Clinical Chemistry. 2001; 47: 667-672.
Li Y et al. Determination of RHD zygosity using real-time quantitative PCR. Swiss Medical Weekly. 2003; 133: 442-445.
Perco P et al. Testing for the D zygosity with three different methods revealed altered Rhsus boxes and a new weak D type. Transfusion. Mar. 2003; 43: 335-339.
Shao CP. [Applications of RHD zygosity test through polymerase chain reaction for prediction of fetus Rh D-positive phenotype]. [Article in Chinese] Zhonghua Fu Chan Ke Za Zhi. Apr. 2003; 38(4): 223-5 (English Abstract).
Shao CP and Xiong W. [A new PCR method for direct determination of RHD zygosity]. [Article in Chinese] Zhonghua Yi Xue Za Zhi. May 2004; 84(9): 736-9 (English Abstract).
Zhou HY et al. [Determination of human RHD gene rhesus box and its significance.] [Article in Chinese] Zhongguo Shi Yan Xue Ye Xue Za Zhi. Feb. 2005; 13(1): 130-4.
Wagner FF et al. Genetic mechanisms of Rhesus box variation. Transfusion. Mar. 2005; 45: 338-344.
Lan JC et al. [A method for Rhesus box test.] [Article in Chinese] Zhongguo Shi Yan Xue Ye Xue Za Zhi. Dec. 2005; 13(6): 1103-5.
Krog GR et al. Quantitation of RHD by real-time polymerase chain reaction for determination of RHD zygosity and RHD mosaicism/chimerism: an evaluation of four quantitative methods. Transfusion. Apr. 2007; 47: 715-722.
Polin H et al. Identification of RHD alleles with the potential of anti-D immunization among seemingly D- blood donors in upper Austria. Transfusion. Apr. 2009; 49: 676-681.
Grootkerk-Tax et al., "The highly variable RH locus in nonwhite persons hampers RHD zygosity determination but yields more insight into RH-related evolutionary events," *Transfusion*, 2005, 45: 327-337.

* cited by examiner

*Primary Examiner* — Young J Kim
(74) *Attorney, Agent, or Firm* — Myers Bigel, P.A.

(57) ABSTRACT

Provided herein are primers comprising a nucleotide sequence complementary to a portion of a RhD gene. Also provided herein are methods of determining a RhD zygosity in a subject. Also provided are methods of detecting a weak D allele in a subject. Further provided are kits for determining an RhD zygosity.

11 Claims, 2 Drawing Sheets

SEQUENCE LISTING

<160> NUMBER OF SEQ ID NOS: 6

<210> SEQ ID NO 1
<211> LENGTH: 21
<212> TYPE: DNA
<213> ORGANISM: Artificial
<220> FEATURE:
<223> OTHER INFORMATION: PCR primer

<400> SEQUENCE: 1
ccacaacgca tgggaattca g                                          21

<210> SEQ ID NO 2
<211> LENGTH: 21
<212> TYPE: DNA
<213> ORGANISM: Artificial
<220> FEATURE:
<223> OTHER INFORMATION: PCR primer

<400> SEQUENCE: 2
aaactgcatg acaatctata g                                          21

<210> SEQ ID NO 3
<211> LENGTH: 27
<212> TYPE: DNA
<213> ORGANISM: Artificial
<220> FEATURE:
<223> OTHER INFORMATION: PCR primer

<400> SEQUENCE: 3 ggttttttttg tttgttttttg gcggtgc                                  27

<210> SEQ ID NO 4
<211> LENGTH: 3069
<212> TYPE: DNA
<213> ORGANISM: Homo sapiens

<400> SEQUENCE: 4
acctgtcccc atgattcagt tacctcccac tgggtccctc ccacaacgca tgggaattca      60
ggatgagatt tgggtgggga cacaaccaaa ccctatcatt ccacccatgg cccctcccaa     120
atttcatgtc ctcacatttc aaaccaatc acaccatccc aacagtccct caaagtctta     180
aatgatttca gcattaactc aaaagtccac agtctaatgt ctcatctgag acaaggcaag     240
tcctttccgt ctatgagcct ataaaatcca aagcaagtta attacttcct agatacaatg     300
ggggtacagg cattgggtaa atacagccat tccaaatggg ataaattggt caaaacaaag     360
aggctacagg cccatgagag tccaaaatcc agtggggcag tcaaatctta aagctccaaa     420
atgatctcct cttgactcca catctcacat ccaggtcatg cagatggaag gggtgggttc     480
ccatggtctt gggcagctct gcccctgtac ctttgcaggg tacagcctcc ctctcagctg     540 cttttcatggg ctggcattga gtgtctgcaa cttttccagg tacacggtgc aagctgtcgg     600
tggatctacc attctggggt ctggaggacc tcttctcaca gctccactag gtggtgcccc     660
agtagggact gtgtgtgggg tctctgaccc cacatttccc ttctgcactg ccctggcaga     720
ggatctccat gagggccctg cccctgcagc aaacttctgc ctgggcatcc aggcatttcc     780
gcacatcctc tttaatctag gcgaaggttt ccaaaccccca gttcttgact tctgtgcact     840
cgcagtctca acaccacatg gaagctgtca aggcttgggg cttgcactcc ccgaagctac     900
agcccaagct ctaccttgcc tcctgtcagt catggttggg agtggctggg atgcagggca     960
ccaagtccct aggctgcaca cagcatgagg accccgggcc tggccaacaa aaccattttt    1020

```
tcctgatatc tctggacctg tgatgggagg ggttgccata aagacctctg acatgccctg    1080
gagacatttt ccccattgtc ttgggaatta gcatttggct cctgttactc atgcaaattt    1140
ctgcagccag cttgaatttc tcctcagaaa atgggaattt ttcttttcta tcacattgtc    1200
aggctgcaaa ttttccgaac ttttatgctc tgcttccctt ataaaactga atgtcttta    1260 cagcacccaa gtcacctctt gaatgctttg ctgcttagaa atttctcctg ccagatactc    1320
taaatcatct ctctgaagtt caaagttcta caaatatctc gtgcaggggc aaaatgccgc    1380
cagtatcttt gctaaaacat aacaagagtc ccctttgctc cagttcccaa caagttcctc    1440
atttccgtct gagaccacct cagcctatgg actttattgt ccacagtgct atcagcattt    1500
tgggcaaagc cattcaacaa gtctctagga agttccaaac tttcccacat ttgcctgtct    1560
tcttctgagc cctccaaact gttccaaacc ctgcctgtta cccagttcca aagtcacata    1620 cccattttg agtatctacg gcagcacccc actctactgg taccaattta gccactgaag     1680
tagttggaga acagaagtaa tagactctgg tttacattgt aaaagcttct ctgtggctgc    1740
tgtgtgaaga aaatatatga gaatgaagcc ccaagatgaa gcagggacac agttgcagtg    1800
gttagagtaa gaaatgctgc tggctggcac tgaagtgata gcctggaggt ttgtgtgtgc    1860
acatgcatgt gtatgtgttt tacgatagta ggcccaacag atactgtaat ccacacttgt    1920
tttttttttt tttttgagac agagtctcac ctgttgccta gactagaatg cagtggcaca    1980
atcttggctc actacaacct ccacctccca ggttcaaaca atccttgtgc ttcagcctcc    2040
cgagtagttg ggattacagg tgtgtgccac cgtgcccagc tatatttttt gtatttttag    2100
cagagatggg attttgccac attggccagg ctggtcttga actcctggcc tcaagcaatc    2160
ctcccacctt agcctcccaa agtgctgagc caccacacct ggccgcaact gattttaat     2220 catgaaatga cacatacatt taaaaaaccc aatacctata atattcctgg ctagtactct    2280
tcacatctat atcatcaaaa acaaagaaag tatgtgaaac tgacacagcc aaggggagac    2340
taaggagaca taacaattaa ctgtaatgtg gtattctgga ggggatcctg gaacagaaaa    2400
agacattagg caaaaaacta agaaatctg aataaaatgt ggatgtcagt taataataat     2460
gtatcatatt agtccagtaa ttgtaacaaa tatacccaat aatgaaagcc attaattata    2520
gggaaaatgg aggggttaat atgggtggct ggcttttgct attttctagca gctccatttt    2580 atctacaaaa gacaaacatt cattaagtcc caaaaaggta agaatgaca aattaagcat      2640 gtatcttatt agtaagagta atataaagat gctcactcat atttataaat atttgacaat    2700
gatgttaagc ccagaaaaga gaaaaaggg taggggcaaa aaacgcaaag agaaggagt       2760 tagtatcttt tctcccgcac tcattagcta ttaaaagagg atgtttgttt aaagctgctc    2820
agagctggta aactaatgtt aagtcactaa cgggaattta aaaggtttca ttaagaactg    2880
cctgcactag attcctccac cctgagacat taaacaatca cgataaacct cctgagtggt    2940
aagaacgtgt ccatttaaaa acaggctata gattgtcatg cagttttatc tactaatcgg    3000
ctaatgcacc gccaaaaaca aacaaaaaaa cccaagggga tgaaagtttc atccatcaaa    3060
ggaaacaac                                                            3069
```

<210> SEQ ID NO 5
<211> LENGTH: 3068
<212> TYPE: DNA
<213> ORGANISM: Homo sapiens

<400> SEQUENCE: 5

-continued

| | | | | |
|---|---|---|---|---|
| acctgtcccc | atgattcagt | tacctcccac | tgggtccctc | ccacaacgca | tgggaattca | 60 |
| ggatgagatt | tgggtgggga | cacaaccaaa | ccctatcatt | ccacccatgg | ccctcccaa | 120 |
| atttcatgtc | ctcacatttc | aaaaccaatc | acaccatccc | aacagtccct | caaagtctta | 180 |
| aatgatttca | gcattaactc | aaaagtccac | agtctaatgt | ctcatctgag | acaaggcaag | 240 |
| tcctttccat | ttatgagcct | ataaaatcca | agcaagtta | gttacttcct | agatacaatg | 300 |
| ggggtacagg | cattgggtaa | atacagccat | tccaaatggg | ataaattggt | caaaacaaag | 360 |
| aggctacagg | cccatgagag | tccaaaatcc | agtggggcag | tcaaatctta | aagctccaaa | 420 |
| atgatctcct | ttgactccac | atctcacatc | caggtcacgc | agatggaagg | ggtgggttcc | 480 |
| catggtcttg | ggcagctctg | cccctgtacc | tttgcagggt | acagcctccc | tctcagctgc | 540 |
| tttcatgggc | tggcattgag | tgtctgcagc | ttttccaggt | acacggtgca | agctgtcggt | 600 |
| ggatctacca | ttctggggtc | tggaggacct | cttctcacag | ctccactagg | tggtgcccca | 660 |
| gtagggactg | tgtgtggggt | ctctgacccc | acatttccct | tctgcactgc | cctggcagag | 720 |
| gatctccatg | agggccctgc | tcctgcagca | aacttctgac | tgggcatcca | ggcatttccg | 780 |
| cacatcctct | ttaatctagg | cgaaggtttc | caaaccccaa | ttcttgactt | ctgtgcactc | 840 |
| gcagtctcaa | caccacatgg | aagctgtcaa | ggcttgggc | ttgcactccc | cgaagctaca | 900 |
| gcccaagctc | taccttgcct | cccgtcagtc | atggttggga | gtggctggga | tgcagggcac | 960 |
| caagtcccta | ggctgcacac | agcatgagga | ccccgggcct | ggccaacaaa | accattttt | 1020 |
| cctgatacct | ctggacctgt | gatgggaggg | gttgccataa | agacctctga | catgccctgg | 1080 |
| agacattttc | cccattgtct | tgggaattag | catttggctc | ctgttactca | tgcaaatttc | 1140 |
| tgcagccagc | ttgaatttct | cctcagaaaa | tgggaatttt | tcttttctat | cacattgtca | 1200 |
| ggctgcaaat | tttccgaact | tttatgctct | gcttccctta | taaaactgaa | tgtcttttaac | 1260 |
| agcacccaag | tcacctcttg | aatgctttgc | tgcttagaaa | tttctcctgc | cagatactct | 1320 |
| aaatcatctc | tctgaagttc | aaagttctac | aaatatctcg | tgcaggggca | aaatgccgcc | 1380 |
| agtatctttg | ctaaaacata | caagagtcc | cctttgctcc | agttcccaac | aagttcctca | 1440 |
| tttccgtctg | agaccacctc | agcctatgga | ctttattgtc | cacagtgcta | tcagcatttt | 1500 |
| gggcaaagcc | attcaacaag | tctctaggaa | gttccaaact | ttcccacatt | tgcctgtctt | 1560 |
| cttctgagcc | ctccaaactg | ttccaaaccc | tgcctgttac | ccagttccaa | agtcacatac | 1620 |
| ccatttttga | gtatctacgg | cagcacccca | ctctactggt | accaatttag | ccactgaagt | 1680 |
| agttggagaa | cagaagtaat | agactctggt | ttacattgta | aaagcttctc | tgtggctgct | 1740 |
| gtgtgaagaa | aatatatgag | aatgaagccc | caagatgaag | cagggacaca | gttgcagtgg | 1800 |
| ttagagtaag | aaatgctgct | ggctggcact | gaagtgatag | cctggaggtt | tgtgtgtgca | 1860 |
| catgcatgtg | tatgtgtttt | acgatagtag | gcccaacaga | tactgtaatc | cacacttgtt | 1920 |
| ttttttttt | ttttgagaca | gagtctcacc | tgttgcctag | actagaatgc | agtggcacaa | 1980 |
| tcttggctca | ctacaacctc | cacctcccag | gttcaaacaa | tccttgtgct | tcagcctccc | 2040 |
| gagtagttgg | gattacaggt | gtgtgccacc | gtgcccagct | atattttttg | tattttttagc | 2100 |
| agagatggga | ttttgccaca | ttggccaggc | tggtcttgaa | ctcctggcct | caagcaatcc | 2160 |
| tcccacctta | gcctcccaaa | gtgctgagcc | accacacctg | gccgcaactg | atttttaatc | 2220 |
| atgaaatgac | acatacattt | aaaaaaccca | atacctataa | tattcctggc | tagtactctt | 2280 |

```
cacatctata tcatcaaaaa caaagaaagt atgtgaaact gacacagcca agggagagact    2340 aaggagacat aacaattaac tgtaatgtgg tattctggag gggatcctgg aacagaaaaa    2400
gacattaggc aaaaaactaa agaaatctga ataaaatgtg gatgtcagtt aataataatg    2460
tatcatatta gtccagtaat tgtaacaaat atacccaata atgaaagcca ttaattatag    2520
ggaaaatgga ggggttaata tgggtggctg gcttttgcta tttctagcag ctccatttta    2580
tctacaaaag acaaacattc attaagtccc aaaaaggtaa agaatgacaa attaagcatg    2640
tatcttatta gtaagagtaa tataaagatg ctcactcata tttataaata tttgacaatg    2700
atgttaaggc cagaaaagag aaaaaagggt aggggcaaaa aacgcaaaga gaaaggagtt    2760
agtatctttt ctcccgcact cattagctat aaaagagga tgtttgttta aagctgctca    2820
gagctggtaa actaatgtta agtcactaac gggaatttaa aaggtttcat taagaactgc    2880
ctgcactaga ttcctccacc ctgagacatt aaacaatcac gataaacctc tgagtggta    2940 agaacgtgtc catttaaaaa caggctatag attgtcatgc agttttatct actaatcggc    3000
taatgcaccg ccaaaaacaa acaaaaaaac ccaaagggat gaaagtttca tccatcaaag    3060
gaaacaac                                                             3068

<210> SEQ ID NO 6
<211> LENGTH: 3063
<212> TYPE: DNA
<213> ORGANISM: Homo sapiens

<400> SEQUENCE: 6
acctgtcccc atgattcagt tacctcccac tgggtccctc ccacaacgca tgggaattca     60
ggatgagatt tgggtgggga cacaaccaaa ccctatcatt ccacccatgg cccctcccaa    120
atttcatgtc ctcacatttc aaaaccaatc acaccatccc aacagtccct caaagtctta    180
aatgatttca gcattaactc aaaagtccac agtctaatgt ctcatctgag acaaggcaag    240
tccttttcat ttatgagcct ataaaatcca aagcaagtta gttacttcct agatacaatg    300
ggggtacagg cattgggtaa atacagccat tccaaatggg ataaattggt caaaacaaag    360
aggctacagg cccatgagag tccaaaatcc agtggggcag tcaaatctta aagctccaaa    420
atgatctcct ttgactccac atctcacatc caggtcacgc agatggaagg ggtgggttcc    480
catggtcttg ggcagctctg cccctgtacc tttgcagggt acagcctccc tctcagctgc    540
tttcatgggc tggcattgag tgtctgcagc ttttccaggt acacggtgca agctgtcggt    600
ggatctacca tttctggggtc tggaggacct cttctcacag ctccactagg tggtgcccca    660
gtagggactg tgtgtggggt ctctgacccc acatttccct tctgcactgc cctggcagag    720
gatctccatg agggccctgc tcctgcagca aacttctgac tgggcatcca ggcatttccg    780
cacatcctct ttaatctagg cgaaggtttc caaaccccaa ttcttgactt ctgtgcactc    840
gcagtctcaa caccacatgg aagctgtcaa ggcttgggc ttgcactccc cgaagctaca    900
gcccaagctc taccttgcct cccgtcagtc atggttggga gtggctggga tgcagggcac    960
caagtcccta ggctgcacac agcatgagga ccccgggcct ggccaacaaa accatttttt   1020
cctgatacct ctggacctgt gatgggaggg gttgccataa agacctctga catgccctgg   1080
agacattttc cccattgtct tgggaattag catttggctc ctgttactca tgcaaatttc    1140
tgcagccagc ttgaatttct cctcagaaaa tgggaatttt tctttctat cacattgtca    1200 ggctgcaaat tttccgaact tttatgctct gcttccctta taaaactgaa tgtctttaac   1260
```

-continued

```
agcacccaag tcacctcttg aatgctttgc tgcttagaaa tttctcctgc cagatactct     1320
aaatcatctc tctgaagttc aaagttctac aaatatctcg tgcaggggca aaatgccgcc     1380
agtatctttg ctaaaacata acaagagtcc cctttgctcc agttcccaac aagttcctca     1440
tttccgtctg agaccacctc agcctatgga ctttattgtc cacagtgcta tcagcatttt     1500
gggcaaagcc attcaacaag tctctaggaa gttccaaact ttcccacatt tgcctgtctt     1560
cttctgagcc ctccaaactg ttccaaaccc tgcctgttac ccagttccaa agtcacatac     1620
ccatttttga gtatctacgg cagcacccca ctctactggt accaatttag ccactgaagt     1680
agttggagaa cagaagtaat agactctggt ttacattgta aaagcttctc tgtggctgct     1740
gtgtgaagaa aatatatgag aatgaagccc caagatgaag cagggacaca gttgcagtgg     1800
ttagagtaag aaatgctgct ggctggcact gaagtgatag cctggaggtt tgtgtgtgca     1860
catgcatgtg tatgtgtttt acgatagtag gcccaacaga tactgtaatc cacacttgtt     1920
tttttttttt gagacagagt ctcacctgtt gcctagacta gaatgcagtg gcacaatctt     1980
ggctcactac aacctccacc tcccaggttc aaacaatcct tgtgcttcag cctcccgagt     2040
agttgggatt acaggtgtgt gccaccgtgc ccagctatat ttttttgtatt tttagcagag   2100 atgggatttt gccacattgg ccaggctggt cttgaactcc tggcctcaag caatcctccc    2160
accttagcct cccaaagtgc tgagccacca cacctggccg caactgattt ttaatcatga    2220
aatgacacat acatttaaaa aacccaatac ctataatatt cctggctagt actcttcaca    2280
tctatatcat caaaaacaaa gaaagtatgt gaaactgaca cagccaaggg gagactaagg    2340
agacataaca attaactgta atgtggtatt ctggagggga tcctggaaca gaaaaagaca    2400
ttaggcaaaa aactaaagaa atctgaataa aatgtggatg tcagttaata ataatgtatc    2460
atattagtcc agtaattgta acaaatatac cacaataatg aaagccatta attataggga    2520
aaatggaggg gttaatatgg gtggctggct tttgctattt ctagcagctc cattttatct    2580
gcaaaagaca aacattcatt aagtcccaaa aaggtaaaga atgacaaatt aagcatgtat    2640
cttattagta agagtaatat aaagatgctc actcctatttt ataaatattt gacaatcatg   2700
ttaaggccac aaaagagaaa aaagggtagg ggcaaaaaac gcaaagagaa aggagttagt    2760
atcttttctc ccgcactcat tagctattaa aagaggatgt ttgtttaaag ctgctcagag    2820
ctggtaaact aatgttaagt cactaacggg aatttaaaag gtttcattaa gaactgcctg    2880
cactagattc ctccaccctg agacattaaa caatcacgat aaacctcctg agtggtaaga    2940
acttgtccat ttaaaaacag gctatagatt gtatcatgca gttttatcta ctaatcggct    3000
aatatcccgc caaaaacaaa aaaccccaaa gggatgaaag tttcatccat caaaggaaac    3060
aac                                                                  3063
```

PRIMERS AND METHODS FOR DETERMINING RHD ZYGOSITY

RELATED APPLICATIONS

This patent application claims the benefit under 35 U.S.C. §119(e) of U.S. Provisional Application No. 61/244,711, filed Sep. 22, 2009, the disclosure of which is hereby incorporated by reference in its entirety.

BACKGROUND

Human blood is classified by antigenic compatibility according to two main systems: the ABO system and Rhesus (Rh) system. The Rh system consists of several closely related proteins encoded by two tandemly duplicated genes on human chromosome 1. Clinically, the most important Rh antigen is called Rhesus D (RhD) antigen. Humans who have this antigen on their red blood cells are termed RhD positive (RhD$^+$), whereas those that do not carry the antigen are termed RhD negative (RhD$^-$). As the Rh blood types are inherited characteristics, a fetus may inherit a blood type from its father that differs from that of its mother. Clinically this is not a problem if the mother is RhD$^+$, but if the mother is RhD$^-$ and the fetus inherits the dominant RhD allele from the father, complications during pregnancy may arise.

SUMMARY

Provided herein are primers comprising a nucleotide having a sequence complementary to a portion of the RhD gene. The primers may include a nucleotide comprising the nucleotide sequence of SEQ ID NO:1, SEQ ID NO:2 or SEQ ID NO:3, or a nucleotide sequence with at least 90, 93, 95, 96, 97, 98, or 99% identity thereto. The primer can, for example, be about 18 to about 30 nucleotides, or about 25 to about 50 nucleotides, in length. For example the primer may be from 15, 16, 17, 18, 19 or 20 nucleotides to 22, 25, 28, 30, 35 or 50 nucleotides in length.

Also provided are methods of determining RhD zygosity in a subject. The methods comprise obtaining a nucleic acid from a biological sample of the subject; performing a polymerase chain reaction (PCR) assay on the nucleic acid with a primer pair comprising a first primer and a second primer, wherein the PCR assay results in a PCR-product; digesting the PCR-product with a restriction enzyme; and analyzing the digested PCR-product for nucleotide fragments of a first, second, or third pattern, wherein the PCR-product pattern determines the RhD zygosity of the subject. The first primer comprises a nucleotide sequence complementary to a portion of a RhD gene, wherein the nucleotide sequence comprises SEQ ID NO:1, SEQ ID NO:2 or SEQ ID NO:3, or a nucleotide sequence with at least 90% identity thereto, and optionally wherein the nucleotide sequence is about 18 to 30 nucleotides in length.

Also provided are methods of detecting a weak D allele in a subject. The methods comprise obtaining a nucleic acid from a biological sample of the subject; performing a polymerase chain reaction (PCR) assay on the nucleic acid with a primer pair comprising a first primer and a second primer, wherein the PCR assay results in a PCR-product; digesting the PCR-product with a restriction enzyme; analyzing the digested PCR-product for nucleotide fragments of a first, second, or third pattern, wherein the digested PCR-product pattern determines the RhD zygosity of the subject; and sequencing the RhD gene to determine if the subject has a weak D allele, wherein a mutation with the RhD gene indicates the subject has a weak D allele. The first primer comprises a nucleotide sequence complementary to a portion of a RhD gene, wherein the nucleotide sequence comprises SEQ ID NO:1, SEQ ID NO:2, or SEQ ID NO:3, or a nucleotide sequence with at least 90% identity thereto, and optionally wherein the nucleotide sequence is about 18 to about 30 nucleotides in length.

Further provided are kits for determining RhD zygosity. The kits comprise a first primer comprising a nucleotide sequence complementary to a portion of the a RhD gene as provided herein, wherein the nucleotide sequence optionally comprises SEQ ID NO:1, SEQ ID NO:2 or SEQ ID NO:3, or a nucleotide sequence with at least 90% identity thereto, and optionally wherein the nucleotide sequence is about 18 to about 30 nucleotides in length; and a container. Optionally, a second primer and/or other components are included in the kit.

DETAILED DESCRIPTION

Provided herein are primers comprising a nucleotide sequence complementary to a portion of a RhD gene. As known in the art, a "primer" is a strand of nucleic acid (DNA, RNA, modified forms thereof, etc.) that may be used, for example, as a starting point for DNA synthesis. The primers may be used in molecular biological techniques such as PCR, hybridization and microarray analysis, etc., and optionally are nucleic acids. Nucleic acids to be used as primers may be synthesized using techniques well known in the art.

The primers may comprise a nucleotide sequence comprising SEQ ID NO:1 or a nucleotide sequence with at least 90% identity to SEQ ID NO:1, and wherein the nucleotide sequence is about 18 to about 30 nucleotides in length. Optionally, the nucleotide sequence comprises about 1 to about 10 nucleotides (or any number of nucleotides in the range) at a 5'-end of SEQ ID NO:1. Optionally, the nucleotide sequence has at least 90% identity to SEQ ID NO:1, Optionally, the nucleotide sequence has at least 95% identity to SEQ ID NO:1. Optionally, the nucleotide sequence has at least 99% identity to SEQ ID NO:1. Optionally, the nucleotide sequence comprises SEQ ID NO:1.

Provided herein are primers comprising a nucleotide sequence complementary to a portion of a RhD gene. The primers comprise a nucleotide sequence comprising SEQ ID NO:2 or a nucleotide sequence with at least 90% identity to SEQ ID NO:2, and wherein the nucleotide sequence is about 25 to about 50 (or any number of nucleotides in the range) nucleotides in length. Optionally, the nucleotide sequence comprises about 1 to about 10 additional nucleotides (or any number of nucleotides in the range) at a 5'-end of SEQ ID NO:2. Optionally, the nucleotide sequence comprises about 1 to about 10 additional nucleotides (or any number of nucleotides in the range) at a 3'-end of SEQ ID NO:2. The nucleotide sequence can, for example, comprise about 1 to about 10 additional nucleotides (or any number of nucleotides in the range) at each of a 5'- and a 3'-end of SEQ ID NO:2. Optionally, the nucleotide sequence has at least 90% identity to SEQ ID NO:2. Optionally, the nucleotide sequence has at least 95% identity to SEQ ID NO:2. Optionally, the nucleotide sequence has at least 99% identity to SEQ ID NO:2. Optionally, the nucleotide sequence comprises SEQ ID NO:2. Optionally, the primer hybridizes to a portion of the RhD gene at stringent conditions.

Also provided herein are primers comprising a nucleotide sequence complementary to a portion of a RhD gene. The primers comprise a nucleotide sequence comprising SEQ ID NO:3 or a nucleotide sequence with at least 93% identity to SEQ ID NO:3, and wherein the nucleotide sequence is about 25 to about 50 nucleotides (or any number of nucleotides in the range) in length. Optionally, the nucleotide sequence comprises about 1 to about 10 additional nucleotides (or any number of nucleotides in the range) at a 5'-end of SEQ ID NO:3. Optionally, the nucleotide sequence comprises about 1 to about 10 additional nucleotides (or any number of nucleotides in the range) at a 3'-end of SEQ ID NO:3. Optionally, the nucleotide sequence comprises about 1 to about 10 additional nucleotides (or any number of nucleotides in the range) at each of a 5'- and a 3'-end of SEQ ID NO:3. Optionally, the nucleotide sequence has at least 93% identity to SEQ ID NO:3. Optionally, the nucleotide sequence has at least 95% identity to SEQ ID NO:3. Optionally, the nucleotide sequence has at least 99% identity to SEQ ID NO:3. Optionally, the nucleotide sequence comprises SEQ ID NO:3. Optionally, the primer hybridizes to a portion of the RhD gene at stringent conditions.

Further provided are methods of determining RhD zygosity in a subject. The methods comprise (a) obtaining a nucleic acid from a biological sample of a subject; (b) performing a polymerase chain reaction (PCR) assay on the nucleic acid with a primer pair comprising (i) a first primer, wherein the first primer comprises a nucleotide sequence complementary to a sequence in a RhD gene, wherein the nucleotide sequence comprises SEQ ID NO:1 or a nucleotide sequence with at least 90% identity to SEQ ID NO:1, and wherein the nucleotide sequence is about 18 to about 30 nucleotides in length, and (ii) a second primer, wherein the PCR assay results in a PCR-product; (c) digesting the PCR-product with a restriction enzyme; and (d) analyzing the digested PCR-product for nucleotide fragments of a first, second, third pattern; wherein the digested PCR-product pattern determines the RhD zygosity of the subject. Optionally, the second primer comprises a nucleotide sequence complementary to a portion of a RhD gene, wherein the nucleotide sequence comprises SEQ ID NO:2 or a nucleotide sequence with at least 90% identity to SEQ ID NO:2, and wherein the nucleotide sequence is about 25 to about 50 nucleotides in length. Optionally, the second primer comprises a nucleotide sequence complementary to a portion of a RhD gene, wherein the nucleotide sequence comprises SEQ ID NO:3 or a nucleotide sequence with at least 93% identity to SEQ ID NO:3, and wherein the nucleotide sequence is about 25 to about 50 nucleotides in length. Optionally, the restriction enzyme is PstI.

Further provided are methods of detecting a weak D allele in a subject. The methods comprise (a) obtaining a nucleic, acid from the a biological sample of the subject; (b) performing a polymerase chain reaction (PCR) assay on the nucleic acid with a primer pair comprising (i) a first primer, wherein the first primer comprises a nucleotide sequence complementary to a sequence in a RhD gene, wherein the nucleotide sequence comprises SEQ ID NO:1 or a nucleotide sequence with at least 90% identity to SEQ ID NO:1, and wherein the nucleotide sequence is about 18 to about 30 nucleotides in length, and (ii) a second primer, wherein the PCR assay results in a PCR-product; (c) digesting the PCR-product with a restriction enzyme; (d) analyzing the digested PCR-product for nucleotide fragments of a first, second, or third pattern, wherein the digested PCR-product determines the RhD zygosity of the subject; and (e) sequencing the RhD gene to determine if the subject has a weak D allele, wherein a mutation within the RhD gene indicates the subject has a weak D allele. Optionally, the second primer comprises a nucleotide sequence complementary to a portion of a RhD gene, wherein the nucleotide sequence comprises SEQ ID NO:2 or a nucleotide sequence with at least 90% identity to SEQ ID NO:2, and wherein the nucleotide sequence is about 25 to about 50 nucleotides in length. Optionally, the second primer comprises a nucleotide sequence complementary to a portion of a RhD gene, wherein the nucleotide sequence comprises SEQ ID NO:3 or a nucleotide sequence with at least 93% identity to SEQ ID NO:3, and wherein the nucleotide sequence is about 25 to about 50 nucleotides in length. Optionally, the restriction enzyme is PstI.

The digested PCR-product can, for example, produce a first pattern, wherein the first pattern indicates the subject is RhD+/+. The first pattern comprises nucleotide fragments resolved on an electrophoresis gel, wherein the nucleotide fragments are about 1800, 740, and 400 base pairs in length, and lacks nucleotide fragments about 560 and 180 base pairs in length.

The digested PCR-product can, for example, produce a second pattern, wherein the second pattern indicates the subject is RhD+/−. The second pattern comprises nucleotide fragments resolved on an electrophoresis gel, wherein the nucleotide fragments are about 1800, 740, 560, 400, and 180 base pairs in length.

The digested PCR-product can, for example, produce a third pattern, wherein the third pattern indicates the subject is RhD−/−. The third pattern comprises nucleotide fragments resolved on an electrophoresis gel, wherein the nucleotide fragments are about 1800, 560, 400, and 180 base pairs in length, and lacks a nucleotide fragment about 740 base pairs in length.

Provided herein are kits for determining RhD zygosity. The kits comprise a first primer described herein and a container. For example, the first primer comprises a nucleotide sequence complementary to a portion of a RhD gene, wherein the nucleotide sequence comprises SEQ ID NO:1 or a nucleotide sequence with at least 90% identity to SEQ ID NO:1, and wherein the nucleotide sequence is about 18 to about 30 nucleotides (or any number of nucleotides in the range) in length. Optionally, the kit further comprises a second primer described herein. For example, the second primer is a nucleotide sequence complementary to a portion of a RhD gene, wherein the nucleotide sequence comprises SEQ ID NO:2 or a nucleotide sequence with at least 90% identity to SEQ ID NO:2, and wherein the nucleotide sequence is about 25 to about 50 nucleotides (or any number of nucleotides in the range) in length. Optionally, the second primer is a nucleotide sequence complementary to a portion of a RhD gene, wherein the nucleotide sequence comprises SEQ ID NO:3 or a nucleotide sequence with at least 93% identity to SEQ ID NO:3, and wherein the nucleotide sequence is about 25 to about 50 nucleotides (or any number of nucleotides in the range) in length.

Optionally, the kit further comprises a reaction vessel comprising one or more components for a polymerase chain reaction (PCR) assay. The one or more components can, for example, comprise one or more of a thermostable polymerase, a buffer solution, and nucleotides for making a PCR-product. Optionally, the kit further comprises a restriction enzyme for digesting the PCR product. The restriction enzyme can, for example, be PstI. Optionally, the kit further comprises a gel to determine a pattern of the digest PCR products.

The kit can, for example, comprise one or more controls for the first, second, or third pattern of digested PCR product. The first pattern indicates a subject is RhD+/+. The second pattern indicates a subject is RhD+/−. The third pattern indicates the subject is RhD−/−. The control for the first pattern can comprise nucleotide fragments resolved on an electrophoresis gel, wherein the nucleotide fragments are about 1800, 740, and 400 base pairs in length, and lacks nucleotide fragments about 560 and 180 base pairs in length. The control for the second pattern can comprise nucleotide fragments resolved on an electrophoresis gel, wherein the nucleotide fragments are about 1800, 740, 560, 400, and 180 base pairs in length. The control for the third pattern can comprise nucleotide fragments resolved on an electrophoresis gel, wherein the nucleotide fragments are about 1800, 560, 400, and 180 base pairs in length, and lacks a nucleotide fragment about 740 base pairs in length.

Also provided are PCR substrates comprising one or more of the primers described herein. The PCR substrate can, for example, be a test tube, a microfuge tube, a PCR tube, or a multiple-well plate.

Specifically, provided herein are primers complementary to a portion of a RhD gene. Optionally, the primer comprises a nucleotide sequence comprising 5'-CCA CAA CGC ATG GGA ATT CAG-3' (SEQ ID NO:1). Optionally, the primer comprises a nucleotide sequence comprising 5'-AAA CTG CAT GAC AAT CTA TAG-3' (SEQ ID NO:2). Optionally, the primer comprises a nucleotide sequence comprising 5'-GGT TTT TTT GTT TGT TTT TGG CGG TGC-3' (SEQ ID NO:3).

As discussed above, the primers provided herein have a desired function. The primers provided herein selectively bind a portion of the RhD gene and amplify a fragment of the RhD gene located between the forward primer and the reverse primer in a polymerase chain reaction (PCR) assay. The amplified portion of the DNA, referred to herein as a PCR product, is then subjected to a restriction digest and analysis. The result of the analysis indicates the RhD zygosity of a subject.

As with all primers, it is understood that additional modifications in the nucleotide sequence can occur that do not alter the function of the primers. Such modifications include addition and deletion of nucleotides from either the 5' or 3' end of the primer. For example, about 1 to about 10 nucleotides can be added to the 5'-end of a primer comprising SEQ ID NO:1. By way of another example, about 1 to about 10 nucleotides can be added to a 5'-end, a 3'-end, or both a 5'-end and a 3'-end of a primer comprising SEQ ID NO:2 or SEQ ID NO:3.

The primers described herein can be further modified so long as the desired function is maintained. It is understood that one way to define any known modifications that might arise, of the disclosed primers herein is through defining the modifications in terms of identity to specific known sequences. Specifically, disclosed are primers which have at least 90, 91, 92, 93, 94, 95, 96, 97, 98, and 99% identity to SEQ ID NO:1 or SEQ ID NO:2. By way of another example, disclosed are primers which have at least 93, 94, 95, 96, 97, 98, and 99% identity to SEQ ID NO:3. Those of skill in the art readily understand how to determine the identity of two nucleotide sequences. For example, the identity can be calculated after aligning the two sequences so that the identity is at its highest level.

Other methods for calculating the identity of nucleic acids can, for example, include the algorithms disclosed in Zuker, Science 244:48-52 (1989); Jaeger et al., Proc. Natl. Acad. Sci. USA 86:7706-7710 (1989); Jaeger et al., Methods Enzymol. 183:281-306 (1989), which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

Provided herein are methods of determining an RhD zygosity in a subject. The methods comprise performing a polymerase chain reaction (PCR) assay on a nucleic acid obtained from a subject. A PCR assay is a technique used to amplify a single or a few copies of DNA across several orders of magnitude, generating thousands to millions of copies of a particular DNA sequence. Specifically, in the methods described herein, the particular DNA sequence spans a portion of the RhD gene. A PCR assay is broken down into three basic steps: (a) a denaturation step to separate each strand of the DNA to be amplified; (b) an annealing step for the primers used to amplify the DNA to anneal to each strand of DNA; (c) and an extension step for a thermostable polymerase to synthesize a DNA strand. These basic steps are carried out at different temperatures for different amounts of time and are repeated for multiple cycles. Optionally, the annealing temperature in the PCR assay is between 54° C. and 65° C. Optionally, the annealing temperature in the PCR assay is 56° C. PCR assays are known in the art. See, e.g., Lutfalla and Uze, Methods Enzymol. 410:386-400 (2006); Lo and Chan, Methods Mol. Biol. 336:1-10 (2006).

Optionally, the nucleic acid is DNA. Optionally, the nucleic acid is RNA. To perform the PCR assay, the RNA is converted to DNA through a technique known as reverse transcription. Reverse transcription is known in the art. See, e.g., Sambrook et al., Molecular Cloning: A Laboratory Manual, 3rd Ed., Cold Spring Harbor Press, Cold Spring Harbor, N.Y. (2001); Khan et al., Biochem. Biophys. Acta. 1423:17-28 (1999).

The PCR assay produces a PCR product. The PCR product is subjected to a restriction digest to produce a particular pattern. Optionally, the PCR product is digested with PstI. The digested PCR product is run on an electrophoresis gel to analyze the pattern produced by the restriction digest. In determining a RhD zygosity by the methods provided herein, the digested PCR products can produce a first, second, or third pattern when resolved on an electrophoresis gel. The electrophoresis gel can, for example, be an agarose gel or a polyacrylamide gel. Methods of using electrophoresis to separate DNA fragments based on size and the gels to be used are well known in the art. See, e.g., Sambrook et al., Molecular Cloning: A Laboratory Manual, $3^{rd}$ Ed., Cold Spring Harbor Press, Cold Spring Harbor, N.Y. (2001).

Provided herein are methods of detecting a weak D allele in a subject. The method comprises obtaining a nucleic acid (e.g., DNA) from a biological sample of the subject; performing a polymerase chain reaction (PCR) assay on the nucleic acid with a primer pair comprising (i) a first primer and second primer described herein, wherein the PCR assay results in a PCR-product; digesting the PCR-product with a restriction enzyme (e.g., PstI); analyzing the digested PCR-product for nucleotide fragments of a first, second, or third pattern, wherein the digested PCR-product pattern determines the RhD zygosity of the subject; and sequencing the RhD gene to determine if the subject has a weak D allele. A mutation within the RhD gene indicates the subject has a weak D allele. The mutation in the weak D allele comprises any mutation within the coding region of the RhD peptide. Mutations in the RhD gene associated with a weak D allele result in a reduced expression of D antigen. Such mutations are described, for example, in Wagner et al., Blood 95:2699-708 (2000), and Polin et al., Transfusion 49:676-81 (2009). The digested PCR-product produces a first pattern, wherein the first pattern indicates the subject is RhD+/+ as described herein; a second pattern, wherein the second pattern indicates the subject is RhD+/− as described herein; or a third pattern, wherein the third pattern indicates the subject is RhD−/− as described herein. The subject can be either a male or a female. The PCR conditions for the method are as described herein.

Nucleic acid duplex or hybrid stability is expressed as the melting temperature or Tm, which is the temperature at which a primer dissociates from a target DNA. This melting temperature is used to define the required stringency conditions. If sequences are identified that are related and substantially identical to the primer, rather than identical, then it is useful to first establish the lowest temperature at which only homologous annealing of the primer and target nucleic acid occurs in the specified PCR reaction conditions. Assuming that a 1% mismatching results in a 1° C. decrease in Tm, the temperature of the primer annealing step in the PCR reaction is reduced accordingly (for example, if sequences having more than 95% identity are sought, the final annealing temperature is decreased by 5° C.). In practice, the change in Tm can be between 0.5 and 1.5° C. per 1% mismatch. Stringent conditions refer to conditions that permit the primer pair to hybridize only to the target nucleic acid sequence to which a primer, having the corresponding wild-type sequence (or its complement) would bind and preferably to produce a unique amplification product. Highly stringent conditions involve annealing temperatures more than 4° C. higher than the predicted annealing temperature of the primer and target nucleic acid in a PCR reaction. Moderately stringent conditions involve annealing temperatures within a range of plus or minus 4° C. of the predicted annealing temperature of the primer and target nucleic acid in a PCR reaction. Calculating a predicted annealing temperature for a primer and its target nucleic acid is known in the art. See, e.g., Deiffenbach et al., General Concepts for PCR Primer Design, in PCR Primer, A Laboratory Manual, Cold Spring Harbor Laboratory Press, Cold Spring Harbor, N.Y., pp 133-155 (1995); Innis and Gelfand, Optimization of PCRs, in PCR protocols, A Guide to Methods and Applications, CRC Press, London, England, pp 5-11 (1994). Salt concentrations of the PCR reaction buffers and temperatures can be varied to achieve the optimal level of identity between the primer and the target nucleic acid. Additional guidance regarding such conditions is readily available in the art, for example, in Sambrook et al., Molecular Cloning: A Laboratory Manual, 3rd Ed., Cold Spring Harbor Press, Cold Spring Harbor, N.Y. (2001).

As used throughout, subject can be a vertebrate, more specifically a mammal (e.g. a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered. Optionally, the subject is male. As used herein, patient or subject may be used interchangeably and can refer to a subject to be tested for RhD zygosity or a weak D allele. The term patient or subject includes humans and veterinary subjects.

As used herein, a biological sample from which a nucleic acid is extracted is a sample derived from a subject and includes, but is not limited to, any cell, tissue, or biological fluid. For example, the biological sample is a sample of colon tissue or cells, ovary tissue or cells, lung tissue or cells, mammary tissue or cells, skin tissue or cells, or brain tissue or cells. Examples of bodily fluids include, but are not limited to, whole blood, serum, urine, saliva, tissue infiltrate, pleural effusions, lung lavage fluid, bronchoalveolar lavage fluid, and the like. The biological fluid may be a cell culture medium or supernatant of cultured cells from the subject.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

General Methods

Polymerase Chain Reaction (PCR) Assay. For the PCR the SuperTaq™ Plus Kit (Ambion division of Applied Biosystems, product #AM2054: Austin, Tex.) was used following the manufacturer's instructions. Reaction volumes were 40 microliters (μl) and 200 nanograms (ng) of genomic DNA were added. Primer concentration was 400 ng of each primer used per reaction. The components were mixed in a PCR tube and the PCR reactions were carried out as follows: The PCR reaction was heated at 96° C. for 2 minutes to denature the double stranded DNA. Then the PCR reactions was heated at 94° C. for 20 seconds (product melting), 56° C. for 20 seconds (primer annealing), and 68°

C. for 4 minutes (product elongation). This was repeated for 35 cycles. After 35 cycles, the PCR reactions were held at 4° C. until analyzed. Special note: the reaction extension temperature can be anywhere from 64 to 76 degrees C. 68° C. is that recommended for use with SuperTaq™ Plus.

PCR assay analysis. A 10 ml aliquot of PCR product was digested with PST I. The PST I enzyme was obtained from NewEngland Biolabs (NEB; Ipswich, Mass.). Reaction conditions were 10 μl of PCR product; 1 μl of NEB buffer 3 and 1 μl of PST I (5 units per μl). Reactions were incubated at 37° C. for 1 hour. Cut and uncut PCR products were analyzed by agarose gel electrophoresis (1% agarose in TAE buffer). Bands were stained with ethidium bromide and visualized by UV illumination.

Results

Figure 1:
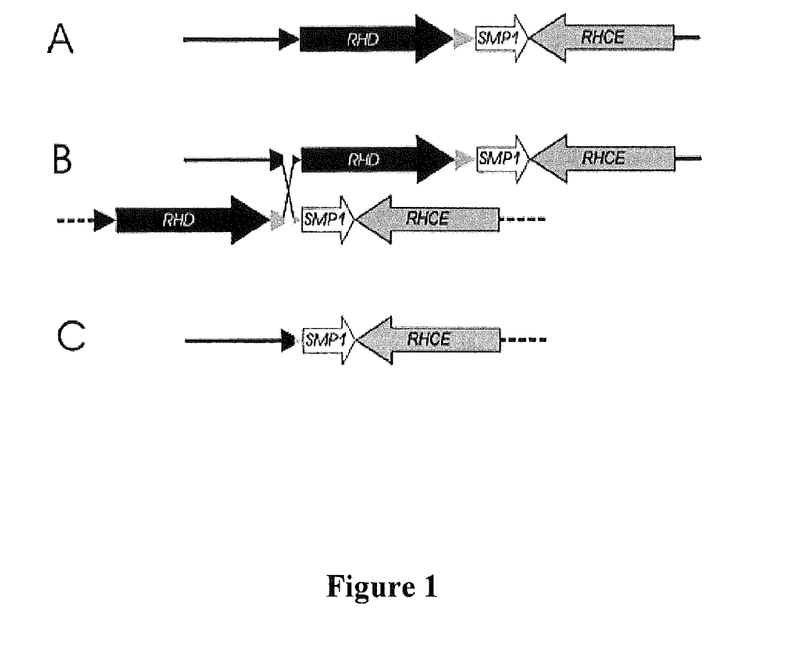
FIG. 1 shows a schematic demonstrating the manner in which the RhD deletion occurred. The RhD deletion resulted from an asymmetrical chromosome crossover.

Although several different mutations are known to confer the RhD− phenotype, the most prevalent is a deletion of the RhD gene that resulted from an asymmetrical chromosome crossover during human evolution. This deletion has become fixed in the human population and is found at highest frequency in the European population. However, it is present in all ethnic groups. FIG. 1 illustrates the way in which the RhD deletion occurred. The RhD gene is followed by a tandem inverted repeat that codes for the RhC and E factors (panel A). An asymmetrical crossover between two nearly identical repeats that flank the RhD gene, indicated by small arrowheads (panel B), resulted in the loss of the RhD gene on one chromosome (panel C) and duplication on the other. The duplication has been lost from the human population but the deletion has become fixed. There are thus two alleles present in the population, one with the RhD gene intact and the other with the RhD gene deleted.

Because of the large size and presence of duplications of the RhD gene and its flanking region, it has proven difficult to design robust genetic assays to identify the presence of both RhD alleles within one individual. As both alleles have been sequenced, a direct comparison of the sequence covering the RhD gene and its deletion can be made. A unique polymorphism that encodes a Pst I restriction site has been identified in the recombinant repeat present on the chromosome carrying the RhD deletion (panel C above). This Pst site can be used to positively identify the presence of the RhD alleles. However, because the repeats flanking the RhD gene and the recombinant repeat are almost identical, it has proven difficult to identify a primer pair that can be used to robustly amplify the sequence flanking the Pst I polymorphism from both alleles. Matters are further complicated by the fact that the repeat sequence flanking the RhD gene can be found throughout the human genome.

TABLE 1

Sequence Alignment for Repeat Boxes Flanking the RhD Gene

| | | |
|---|---|---|
| RhDbox2 | ACCTGTCCCCATGATTCAGTTACCTCCCACTGGGTCCCTCCACAACGCATGGGAATTCA | 60 |
| RhDboxhyb | ACCTGTCCCCATGATTCAGTTACCTCCCACTGGGTCCCTCCACAACGCATGGGAATTCA | 60 |
| RhDbox1 | ACCTGTCCCCATGATTCAGTTACCTCCCACTGGGTCCCTCCACAACGCATGGGAATTCA | 60 |
| RhDbox2 | GGATGAGATTTGGGTGGGGACACAACCAAACCCTATCATTCCACCCATGGCCCCTCCCAA | 120 |
| RhDboxhyb | GGATGAGATTTGGGTGGGGACACAACCAAACCCTATCATTCCACCCATGGCCCCTCCCAA | 120 |
| RhDbox1 | GGATGAGATTTGGGTGGGGACACAACCAAACCCTATCATTCCACCCATGGCCCCTCCCAA | 120 |
| RhDbox2 | ATTTCATGTCCTCACATTTCAAAACCAATCACACCATCCCAACAGTCCCTCAAAGTCTTA | 180 |
| RhDboxhyb | ATTTCATGTCCTCACATTTCAAAACCAATCACACCATCCCAACAGTCCCTCAAAGTCTTA | 180 |
| RhDbox1 | ATTTCATGTCCTCACATTTCAAAACCAATCACACCATCCCAACAGTCCCTCAAAGTCTTA | 180 |
| RhDbox2 | AATGATTTCAGCATTAACTCAAAAGTCCACAGTCTAATGTCTCATCTGAGACAAGGCAAG | 240 |
| RhDbox-hyb | AATGATTTCAGCATTAACTCAAAAGTCCACAGTCTAATGTCTCATCTGAGACAAGGCAAG | 240 |
| RhDbox1 | AATGATTTCAGCATTAACTCAAAAGTCCACAGTCTAATGTCTCATCTGAGACAAGGCAAG | 240 |
| RhDbox2 | TCCTTTCCGTCTATGAGCCTATAAAATCCAAAGCAAGTTAATTACTTCCTAGATACAATG | 300 |
| RhDboxhyb | TCCTTTCCATTTATGAGCCTATAAAATCCAAAGCAAGTTAGTTACTTCCTAGATACAATG | 300 |
| RhDbox1 | TCCTTTCCATTTATGAGCCTATAAAATCCAAAGCAAGTTAGTTACTTCCTAGATACAATG | 300 |
| RhDbox2 | GGGGTACAGGCATTGGGTAAATACAGCCATTCCAAATGGGATAAATTGGTCAAAACAAAG | 360 |
| RhDboxhyb | GGGGTACAGGCATTGGGTAAATACAGCCATTCCAAATGGGATAAATTGGTCAAAACAAAG | 360 |
| RhDbox1 | GGGGTACAGGCATTGGGTAAATACAGCCATTCCAAATGGGATAAATTGGTCAAAACAAAG | 360 |
| RhDbox2 | AGGCTACAGGCCCATGAGAGTCCAAAATCCAGTGGGGCAGTCAAATCTTAAAGCTCCAAA | 420 |
| RhDboxhyb | AGGCTACAGGCCCATGAGAGTCCAAAATCCAGTGGGGCAGTCAAATCTTAAAGCTCCAAA | 420 |
| RhDbox1 | AGGCTACAGGCCCATGAGAGTCCAAAATCCAGTGGGGCAGTCAAATCTTAAAGCTCCAAA | 420 |
| RhDbox2 | ATGATCTCCTCTTGACTCCACATCTCACATCCAGGTCATGCAGATGGAAGGGGTGGGTTC | 480 |
| RhDboxhyb | ATGATCTCCT-TTGACTCCACATCTCACATCCAGGTCACGCAGATGGAAGGGGTGGGTTC | 479 |
| RhDbox1 | ATGATCTCCT-TTGACTCCACATCTCACATCCAGGTCACGCAGATGGAAGGGGTGGGTTC | 479 |
| RhDbox2 | CCATGGTCTTGGGCAGCTCTGCCCCTGTACCTTTGCAGGGTACAGCCTCCCTCTCAGCTG | 540 |
| RhDboxhyb | CCATGGTCTTGGGCAGCTCTGCCCCTGTACCTTTGCAGGGTACAGCCTCCCTCTCAGCTG | 539 |
| RhDbox1 | CCATGGTCTTGGGCAGCTCTGCCCCTGTACCTTTGCAGGGTACAGCCTCCCTCTCAGCTG | 539 |
| RhDbox2 | CTTTCATGGGCTGGCATTGAGTGTCTGCAACTTTTCCAGGTACACGGTGCAAGCTGTCGG | 600 |
| RhDboxhyb | CTTTCATGGGCTGGCATTGAGTGTCTGCAGCTTTTCCAGGTACACGGTGCAAGCTGTCGG | 599 |
| RhDbox1 | CTTTCATGGGCTGGCATTGAGTGTCTGCAGCTTTTCCAGGTACACGGTGCAAGCTGTCGG | 599 |
| RhDbox2 | TGGATCTACCATTCTGGGGTCTGGAGGACCTCTTCTCACAGCTCCACTAGGTGGTGCCCC | 660 |
| RhDboxhyb | TGGATCTACCATTCTGGGGTCTGGAGGACCTCTTCTCACAGCTCCACTAGGTGGTGCCCC | 659 |
| RhDbox1 | TGGATCTACCATTCTGGGGTCTGGAGGACCTCTTCTCACAGCTCCACTAGGTGGTGCCCC | 659 |

TABLE 1-continued

Sequence Alignment for Repeat Boxes Flanking the RhD Gene

```
RhDbox2    AGTAGGGACTGTGTGTGGGGTCTCTGACCCCACATTTCCCTTCTGCACTGCCCTGGCAGA  720
RhDboxhyb  AGTAGGGACTGTGTGTGGGGTCTCTGACCCCACATTTCCCTTCTGCACTGCCCTGGCAGA  719
RhDbox1    AGTAGGGACTGTGTGTGGGGTCTCTGACCCCACATTTCCCTTCTGCACTGCCCTGGCAGA  719

RhDbox2    GGATCTCCATGAGGGCCCTGCCCCTGCAGCAAACTTCTGCCTGGGCATCCAGGCATTTCC  780
RhDboxhyb  GGATCTCCATGAGGGCCCTGCTCCTGCAGCAAACTTCTGACTGGGCATCCAGGCATTTCC  779
RhDbox1    GGATCTCCATGAGGGCCCTGCTCCTGCAGCAAACTTCTGACTGGGCATCCAGGCATTTCC  779

RhDbox2    GCACATCCTCTTTAATCTAGGCGAAGGTTTCCAAACCCCAGTTCTTGACTTCTGTGCACT  840
RhDboxhyb  GCACATCCTCTTTAATCTAGGCGAAGGTTTCCAAACCCCAATTCTTGACTTCTGTGCACT  839
RhDbox1    GCACATCCTCTTTAATCTAGGCGAAGGTTTCCAAACCCCAATTCTTGACTTCTGTGCACT  839

RhDbox2    CGCAGTCTCAACACCACATGGAAGCTGTCAAGGCTTGGGGCTTGCACTCCCCGAAGCTAC  900
RhDboxhyb  CGCAGTCTCAACACCACATGGAAGCTGTCAAGGCTTGGGGCTTGCACTCCCCGAAGCTAC  899
RhDbox1    CGCAGTCTCAACACCACATGGAAGCTGTCAAGGCTTGGGGCTTGCACTCCCCGAAGCTAC  899

RhDbox2    AGCCCAAGCTCTACCTTGCCTCCTGTCAGTCATGGTTGGGAGTGGCTGGGATGCAGGGCA  960
RhDboxhyb  AGCCCAAGCTCTACCTTGCCTCCCGTCAGTCATGGTTGGGAGTGGCTGGGATGCAGGGCA  959
RhDbox1    AGCCCAAGCTCTACCTTGCCTCCCGTCAGTCATGGTTGGGAGTGGCTGGGATGCAGGGCA  959

RhDbox2    CCAAGTCCCTAGGCTGCACACAGCATGAGGACCCCGGGCCTGGCCAACAAAACCATTTTT  1020
RhDboxhyb  CCAAGTCCCTAGGCTGCACACAGCATGAGGACCCCGGGCCTGGCCAACAAAACCATTTTT  1019
RhDbox1    CCAAGTCCCTAGGCTGCACACAGCATGAGGACCCCGGGCCTGGCCAACAAAACCATTTTT  1019

RhDbox2    TCCTGATATCTCTGGACCTGTGATGGGAGGGGTTGCCATAAAGACCTCTGACATGCCCTG  1080
RhDboxhyb  TCCTGATACCTCTGGACCTGTGATGGGAGGGGTTGCCATAAAGACCTCTGACATGCCCTG  1079
RhDbox1    TCCTGATACCTCTGGACCTGTGATGGGAGGGGTTGCCATAAAGACCTCTGACATGCCCTG  1079

RhDbox2    GAGACATTTTCCCCATTGTCTTGGGAATTAGCATTTGGCTCCTGTTACTCATGCAAATTT  1140
RhDboxhyb  GAGACATTTTCCCCATTGTCTTGGGAATTAGCATTTGGCTCCTGTTACTCATGCAAATTT  1139
RhDbox1    GAGACATTTTCCCCATTGTCTTGGGAATTAGCATTTGGCTCCTGTTACTCATGCAAATTT  1139

RhDbox2    CTGCAGCCAGCTTGAATTTCTCCTCAGAAAATGGGAATTTTCTTTTCTATCACATTGTC  1200
RhDboxhyb  CTGCAGCCAGCTTGAATTTCTCCTCAGAAAATGGGAATTTTCTTTTCTATCACATTGTC  1199
RhDbox1    CTGCAGCCAGCTTGAATTTCTCCTCAGAAAATGGGAATTTTCTTTTCTATCACATTGTC  1199

RhDbox2    AGGCTGCAAATTTTCCGAACTTTTATGCTCTGCTTCCCTTATAAAACTGAATGTCTTTAA  1260
RhDboxhyb  AGGCTGCAAATTTTCCGAACTTTTATGCTCTGCTTCCCTTATAAAACTGAATGTCTTTAA  1259
RhDbox1    AGGCTGCAAATTTTCCGAACTTTTATGCTCTGCTTCCCTTATAAAACTGAATGTCTTTAA  1259

RhDbox2    CAGCACCCAAGTCACCTCTTGAATGCTTTGCTGCTTAGAAATTTCTCCTGCCAGATACTC  1320
RhDbox-    CAGCACCCAAGTCACCTCTTGAATGCTTTGCTGCTTAGAAATTTCTCCTGCCAGATACTC  1319
hyb
RhDbox1    CAGCACCCAAGTCACCTCTTGAATGCTTTGCTGCTTAGAAATTTCTCCTGCCAGATACTC  1319

RhDbox2    TAAATCATCTCTCTGAAGTTCAAAGTTCTACAAATATCTCGTGCAGGGGCAAAATGCCGC  1380
RhDbox-    TAAATCATCTCTCTGAAGTTCAAAGTTCTACAAATATCTCGTGCAGGGGCAAAATGCCGC  1379
hyb
RhDbox1    TAAATCATCTCTCTGAAGTTCAAAGTTCTACAAATATCTCGTGCAGGGGCAAAATGCCGC  1379

RhDbox2    CAGTATCTTTGCTAAAACATAACAAGAGTCCCCTTTGCTCCAGTTCCCAACAAGTTCCTC  1440
RhDboxhyb  CAGTATCTTTGCTAAAACATAACAAGAGTCCCCTTTGCTCCAGTTCCCAACAAGTTCCTC  1439
RhDbox1    CAGTATCTTTGCTAAAACATAACAAGAGTCCCCTTTGCTCCAGTTCCCAACAAGTTCCTC  1439

RhDbox2    ATTTCCGTCTGAGACCACCTCAGCCTATGGACTTTATTGTCCACAGTGCTATCAGCATTT  1500
RhDboxhyb  ATTTCCGTCTGAGACCACCTCAGCCTATGGACTTTATTGTCCACAGTGCTATCAGCATTT  1499
RhDbox1    ATTTCCGTCTGAGACCACCTCAGCCTATGGACTTTATTGTCCACAGTGCTATCAGCATTT  1499

RhDbox2    TGGGCAAAGCCATTCAACAAGTCTCTAGGAAGTTCCAAACTTTCCCACATTTGCCTGTCT  1560
RhDbox-    TGGGCAAAGCCATTCAACAAGTCTCTAGGAAGTTCCAAACTTTCCCACATTTGCCTGTCT  1559
hyb
RhDbox1    TGGGCAAAGCCATTCAACAAGTCTCTAGGAAGTTCCAAACTTTCCCACATTTGCCTGTCT  1559

RhDbox2    TCTTCTGAGCCCTCCAAACTGTTCCAAACCCTGCCTGTTACCCAGTTCCAAAGTCACATA  1620
RhDboxhyb  TCTTCTGAGCCCTCCAAACTGTTCCAAACCCTGCCTGTTACCCAGTTCCAAAGTCACATA  1619
RhDbox1    TCTTCTGAGCCCTCCAAACTGTTCCAAACCCTGCCTGTTACCCAGTTCCAAAGTCACATA  1619

RhDbox2    CCCATTTTTGAGTATCTACGGCAGCACCCCACTCTACTGGTACCAATTTAGCCACTGAAG  1680
RhDboxhyb  CCCATTTTTGAGTATCTACGGCAGCACCCCACTCTACTGGTACCAATTTAGCCACTGAAG  1679
RhDbox1    CCCATTTTTGAGTATCTACGGCAGCACCCCACTCTACTGGTACCAATTTAGCCACTGAAG  1679
```

TABLE 1-continued

Sequence Alignment for Repeat Boxes Flanking the RhD Gene

```
RhDbox2     TAGTTGGAGAACAGAAGTAATAGACTCTGGTTTACATTGTAAAAGCTTCTCTGTGGCTGC  1740
RhDbox-     TAGTTGGAGAACAGAAGTAATAGACTCTGGTTTACATTGTAAAAGCTTCTCTGTGGCTGC  1739
hyb
RhDbox1     TAGTTGGAGAACAGAAGTAATAGACTCTGGTTTACATTGTAAAAGCTTCTCTGTGGCTGC  1739

RhDbox2     TGTGTGAAGAAAATATATGAGAATGAAGCCCCAAGATGAAGCAGGGACACAGTTGCAGTG  1800
RhDboxhyb   TGTGTGAAGAAAATATATGAGAATGAAGCCCCAAGATGAAGCAGGGACACAGTTGCAGTG  1799
RhDbox1     TGTGTGAAGAAAATATATGAGAATGAAGCCCCAAGATGAAGCAGGGACACAGTTGCAGTG  1799

RhDbox2     GTTAGAGTAAGAAATGCTGCTGGCTGGCACTGAAGTGATAGCCTGGAGGTTTGTGTGTGC  1860
RhDboxhyb   GTTAGAGTAAGAAATGCTGCTGGCTGGCACTGAAGTGATAGCCTGGAGGTTTGTGTGTGC  1859
RhDbox1     GTTAGAGTAAGAAATGCTGCTGGCTGGCACTGAAGTGATAGCCTGGAGGTTTGTGTGTGC  1859

RhDbox2     ACATGCATGTGTATGTGTTTTACGATAGTAGGCCCAACAGATACTGTAATCCACACTTGT  1920
RhDboxhyb   ACATGCATGTGTATGTGTTTTACGATAGTAGGCCCAACAGATACTGTAATCCACACTTGT  1919
RhDbox1     ACATGCATGTGTATGTGTTTTACGATAGTAGGCCCAACAGATACTGTAATCCACACTTGT  1919

RhDbox2     TTTTTTTTTTTTTTGAGACAGAGTCTCACCTGTTGCCTAGACTAGAATGCAGTGGCACA   1980
RhDboxhyb   TTTTTTTTTTTTTTGAGACAGAGTCTCACCTGTTGCCTAGACTAGAATGCAGTGGCACA   1979
RhDbox1     TTTTTTTTTTT----GAGACAGAGTCTCACCTGTTGCCTAGACTAGAATGCAGTGGCACA   1975

RhDbox2     ATCTTGGCTCACTACAACCTCCACCTCCCAGGTTCAAACAATCCTTGTGCTTCAGCCTCC  2040
RhDboxhyb   ATCTTGGCTCACTACAACCTCCACCTCCCAGGTTCAAACAATCCTTGTGCTTCAGCCTCC  2039
RhDbox1     ATCTTGGCTCACTACAACCTCCACCTCCCAGGTTCAAACAATCCTTGTGCTTCAGCCTCC  2035

RhDbox2     CGAGTAGTTGGGATTACAGGTGTGTGCCACCGTGCCCAGCTATATTTTTTGTATTTTTAG  2100
RhDboxhyb   CGAGTAGTTGGGATTACAGGTGTGTGCCACCGTGCCCAGCTATATTTTTTGTATTTTTAG  2099
RhDbox1     CGAGTAGTTGGGATTACAGGTGTGTGCCACCGTGCCCAGCTATATTTTTTGTATTTTTAG  2095

RhDbox2     CAGAGATGGGATTTTGCCACATTGGCCAGGCTGGTCTTGAACTCCTGGCCTCAAGCAATC  2160
RhDboxhyb   CAGAGATGGGATTTTGCCACATTGGCCAGGCTGGTCTTGAACTCCTGGCCTCAAGCAATC  2159
RhDbox1     CAGAGATGGGATTTTGCCACATTGGCCAGGCTGGTCTTGAACTCCTGGCCTCAAGCAATC  2155

RhDbox2     CTCCCACCTTAGCCTCCCAAAGTGCTGAGCCACCACACCTGGCCGCAACTGATTTTTAAT  2220
RhDboxhyb   CTCCCACCTTAGCCTCCCAAAGTGCTGAGCCACCACACCTGGCCGCAACTGATTTTTAAT  2219
RhDbox1     CTCCCACCTTAGCCTCCCAAAGTGCTGAGCCACCACACCTGGCCGCAACTGATTTTTAAT  2215

RhDbox2     CATGAAATGACACATACATTTAAAAAACCCAATACCTATAATATTCCTGGCTAGTACTCT  2280
RhDboxhyb   CATGAAATGACACATACATTTAAAAAACCCAATACCTATAATATTCCTGGCTAGTACTCT  2279
RhDbox1     CATGAAATGACACATACATTTAAAAAACCCAATACCTATAATATTCCTGGCTAGTACTCT  2275

RhDbox2     TCACATCTATATCATCAAAAACAAAGAAAGTATGTGAAACTGACACAGCCAAGGGGAGAC  2340
RhDboxhyb   TCACATCTATATCATCAAAAACAAAGAAAGTATGTGAAACTGACACAGCCAAGGGGAGAC  2339
RhDbox1     TCACATCTATATCATCAAAAACAAAGAAAGTATGTGAAACTGACACAGCCAAGGGGAGAC  2335

RhDbox2     TAAGGAGACATAACAATTAACTGTAATGTGGTATTCTGGAGGGGATCCTGGAACAGAAAA  2400
RhDboxhyb   TAAGGAGACATAACAATTAACTGTAATGTGGTATTCTGGAGGGGATCCTGGAACAGAAAA  2399
RhDbox1     TAAGGAGACATAACAATTAACTGTAATGTGGTATTCTGGAGGGGATCCTGGAACAGAAAA  2395

RhDbox2     AGACATTAGGCAAAAAACTAAAGAAATCTGAATAAAATGTGGATGTCAGTTAATAATAAT  2460
RhDboxhyb   AGACATTAGGCAAAAAACTAAAGAAATCTGAATAAAATGTGGATGTCAGTTAATAATAAT  2459
RhDbox1     AGACATTAGGCAAAAAACTAAAGAAATCTGAATAAAATGTGGATGTCAGTTAATAATAAT  2455

RhDbox2     GTATCATATTAGTCCAGTAATTGTAACAAATATACC-CAATAATGAAAGCCATTAATTAT  2519
RhDboxhyb   GTATCATATTAGTCCAGTAATTGTAACAAATATACC-CAATAATGAAAGCCATTAATTAT  2518
RhDbox1     GTATCATATTAGTCCAGTAATTGTAACAAATATACCACAATAATGAAAGCCATTAATTAT  2515

RhDbox2     AGGGAAAATGGAGGGGTTAATATGGGTGGCTGGCTTTTGCTATTTCTAGCAGCTCCATTT  2579
RhDboxhyb   AGGGAAAATGGAGGGGTTAATATGGGTGGCTGGCTTTTGCTATTTCTAGCAGCTCCATTT  2578
RhDbox1     AGGGAAAATGGAGGGGTTAATATGGGTGGCTGGCTTTTGCTATTTCTAGCAGCTCCATTT  2575

RhDbox2     TATCTACAAAAGACAAACATTCATTAAGTCCCAAAAAGGTAAAGAATGACAAATTAAGCA  2639
RhDboxhyb   TATCTACAAAAGACAAACATTCATTAAGTCCCAAAAAGGTAAAGAATGACAAATTAAGCA  2638
RhDbox1     TATCTGCAAAAGACAAACATTCATTAAGTCCCAAAAAGGTAAAGAATGACAAATTAAGCA  2635

RhDbox2     TGTATCTTATTAGTAAGAGTAATATAAAGATGCTCACTCATATTTATAAATATTTGACAA  2699
RhDboxhyb   TGTATCTTATTAGTAAGAGTAATATAAAGATGCTCACTCATATTTATAAATATTTGACAA  2698
RhDbox1     TGTATCTTATTAGTAAGAGTAATATAAAGATGCTCACTCCTATTTATAAATATTTGACAA  2695

RhDbox2     TGATGTTAAGGCCAGAAAAGAGAAAAAAGGGTAGGGGCAAAAAACGCAAAGAGAAAGGAG  2759
RhDboxhyb   TGATGTTAAGGCCAGAAAAGAGAAAAAAGGGTAGGGGCAAAAAACGCAAAGAGAAAGGAG  2758
RhDbox1     TCATGTTAAGGCCACAAAAGAGAAAAAAGGGTAGGGGCAAAAAACGCAAAGAGAAAGGAG  2755
```

TABLE 1-continued

Sequence Alignment for Repeat Boxes Flanking the RhD Gene

```
RhDbox2    TTAGTATCTTTTCTCCCGCACTCATTAGCTATTAAAAGAGGATGTTTGTTTAAAGCTGCT  2819
RhDboxhyb  TTAGTATCTTTTCTCCCGCACTCATTAGCTATTAAAAGAGGATGTTTGTTTAAAGCTGCT  2818
RhDbox1    TTAGTATCTTTTCTCCCGCACTCATTAGCTATTAAAAGAGGATGTTTGTTTAAAGCTGCT  2815

RhDbox2    CAGAGCTGGTAAACTAATGTTAAGTCACTAACGGGAATTTAAAAGGTTTCATTAAGAACT  2879
RhDboxhyb  CAGAGCTGGTAAACTAATGTTAAGTCACTAACGGGAATTTAAAAGGTTTCATTAAGAACT  2878
RhDbox1    CAGAGCTGGTAAACTAATGTTAAGTCACTAACGGGAATTTAAAAGGTTTCATTAAGAACT  2875

RhDbox2    GCCTGCACTAGATTCCTCCACCCTGAGACATTAAACAATCACGATAAACCTCCTGAGTGG  2939
RhDboxhyb  GCCTGCACTAGATTCCTCCACCCTGAGACATTAAACAATCACGATAAACCTCCTGAGTGG  2938
RhDbox1    GCCTGCACTAGATTCCTCCACCCTGAGACATTAAACAATCACGATAAACCTCCTGAGTGG  2935

RhDbox2    TAAGAACGTGTCCATTTAAAAACAGGCTATAGATTGT--CATGCAGTTTTATCTACTAAT  2997
RhDboxhyb  TAAGAACGTGTCCATTTAAAAACAGGCTATAGATTGT--CATGCAGTTTTATCTACTAAT  2996
RhDbox1    TAAGAACTTGTCCATTTAAAAACAGGCTATAGATTGTATCATGCAGTTTTATCTACTAAT  2995

RhDbox2    CGGCTAATGCACCGCCAAAAACAAACAAAAAAAACCCAAAGGGATGAAAGTTTCATCCATC  3057
RhDboxhyb  CGGCTAATGCACCGCCAAAAACAAACAAAAAAAACCCAAAGGGATGAAAGTTTCATCCATC  3056
RhDbox1    CGGCTAATATCCCGCCAAAAACAAA----AAACCCCAAAGGGATGAAAGTTTCATCCATC  3051

RhDbox2                                                           SEQ ID NO: 4
           AAAGGAAACAAC  3069

RhDboxhyb                                                         SEQ ID NO: 5
           AAAGGAAACAAC  3068

RhDbox1                                                           SEQ ID NO: 6
           AAAGGAAACAAC  3063
```

As can be seen from the sequence alignment in Table 1, the two repeat boxes flanking the RhD gene (RhDbox1 and RhDbox2) and the hybrid box (RhDboxhyb) are almost identical. The Pst I site that can be used for allelic discrimination is found upstream of base number 600 and is indicated in italics and bold above (base pairs 564-569 of the RhDboxhyb). Two other Pst I sites within the sequence are also indicated in italics and bold (base pairs 742-747 and 1140-1145 of the RhDboxhyb). Because RhD box 1 and the hybrid box both carry the Pst I restriction site up stream of base number 600, a method for only amplifying DNA from RhD box2 and the hybrid box was developed. This allows the absence of the Pst I site to be the marker for the intact RhD gene and the presence of the Pst I site to be used as the marker for the deleted RhD gene. The sequence immediately upstream from base 3057 in the above sequences shows a divergence between RhDbox1 and the other RhDboxes. The sequence divergence consists of base substitutions and deletions. Designing a primer across this divergence (indicated in italics and bold in the above sequence alignment at base pairs 3005-3030 of the RhDboxhyb, SEQ ID NO:3) allowed for the generation of PCR products specific to RhDbox2 and the hybrid box. This primer is unique to the RhD gene and was therefore ideal for use in an assay that is dependent on generating a unique PCR product from genomic DNA. Additionally, a second primer upstream of the 3' primer can be used. It is also indicated in italics and bold at base pairs 2965-2985 of RhDboxhyb (SEQ ID NO:2). In addition to the primer at the end of the sequence of interest a primer at the start of the sequence is required for successful assay development. One such primer was developed and is indicated in italics and bold at base pairs 43-61 of RhDboxhyb (SEQ ID NO:1). As in the previous case, this primer is unique to the RhDboxes and, when used in combination with the previously described primers, led to the production of unique PCR products from human genomic DNA. Previous attempts to achieve this that have been reported in the literature have failed to yield unique PCR product from genomic DNA.

Figure 2:
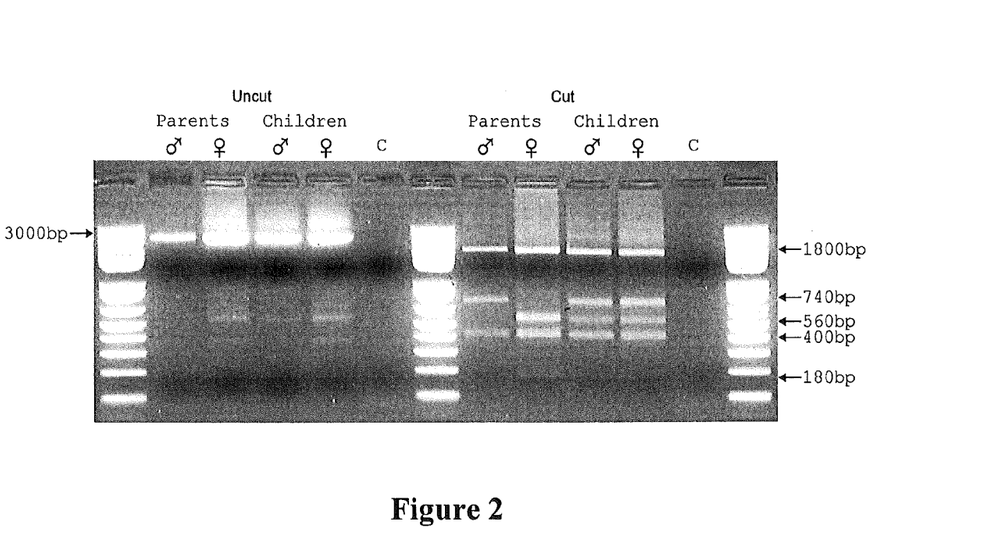
FIG. 2 shows an image of a gel demonstrating the RhD zygosity of several subjects in the same family.

FIG. 2 illustrates the use of the test to determine the zygosity of an RhD−/− mother, RhD+/+ homozygous father and two RhD+/− heterozygous offspring. The left side of the panel shows the uncut PCR product from the parents and offspring, which is approximately 3000 base pairs in size. On the right side, the PCR product was cut with Pst I. The PCR product from the homozygous RhD+/+ father was cut into three bands (two restriction sites) that are 1800, 740 and 400 base pairs in size. The PCR product from the homozygous RhD−/− deletion carrying mother was cut into four bands (three restriction sites) that are 1800, 560, 400 and 180 base pairs in size. The 180 base pair band was not as clearly visible as the others because it contained less DNA that the other bands such that less ethidium bromide was bound even though the molar ratio of the bands was the same. The offspring, one male and one female, were antigenically RhD+/− and heterozygous for the RhD deletion. As a result Pst I digestion of the PCR product obtained from their DNA yielded 5 bands. The 1800 and 400 base pair bands, which they share with both parents, a 740 base pair band, which was diagnostic for the intact RhD allele and two bands of 560 and 180 base pairs, which were diagnostic for the RhD deletion allele.

Figure 3:
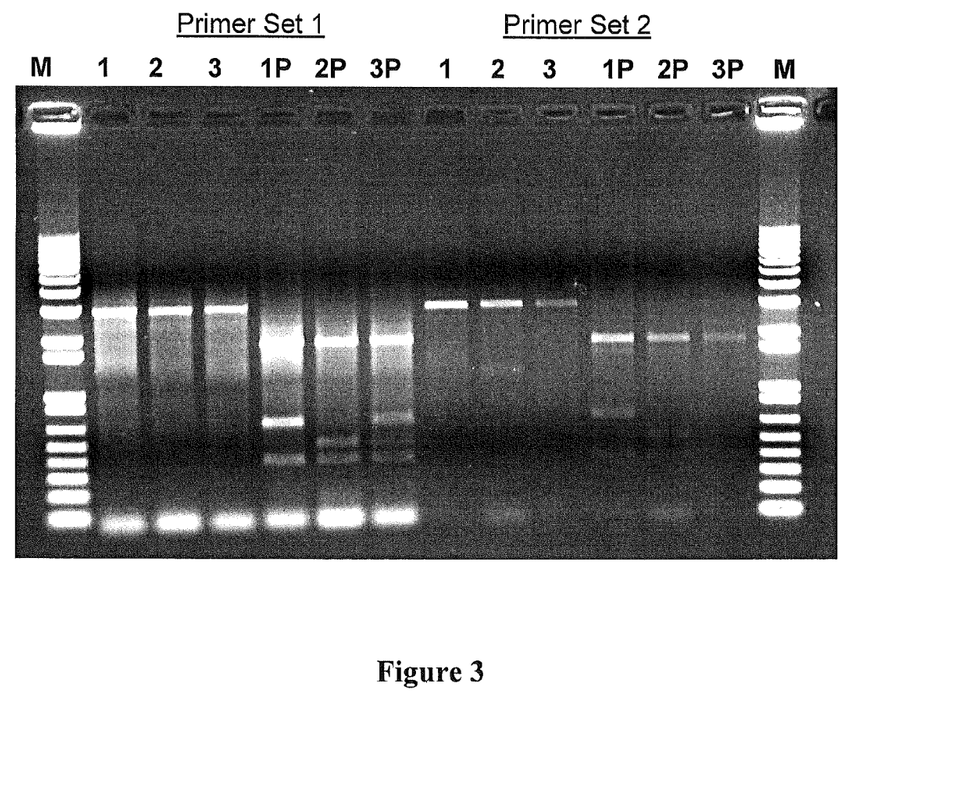
FIG. 3 shows an image of a gel demonstrating the RhD zygosity for RhD+/+, RhD−/−, and RhD+/− subjects with multiple primer pairs. Sample 1: Homozygous RhD+/+; Sample 2: Homozygous RhD−/−; Sample 3: Heterozygous RhD+/−. P indicates sample treated with the restriction enzyme PstI to generate the diagnostic DNA banding pattern.

In addition, a second set of primers was tested which consisted of the original 5' primer and the alternative 3' primer. The second primer set gave less PCR product that the original set under identical test conditions, as evidenced in FIG. 3. However, the second primer set also discriminated between RhD+/+, RhD+/−, and RhD−/− digested PCR products demonstrating that the second primer set could also be used to determine RhD zygosity.

That which is claimed is:

1. A method of determining Rhesus D (RhD) zygosity in a subject, the method comprising:
   (a) obtaining a nucleic acid comprising a RhD gene from a biological sample of the subject;
   (b) performing a PCR assay on the nucleic acid with a primer pair comprising
      (i) a first primer comprising a nucleotide sequence with at least 93% identity to SEQ ID NO:1, wherein the primer is 20 to 31 nucleotides in length, and
      (ii) a second primer, wherein said second primer hybridizes under stringent conditions to a nucleotide sequence in the region between positions 2940 and 3057 of SEQ ID NO:4, SEQ ID NO:5 or SEQ ID NO:6,
   wherein the PCR assay results in a PCR product;
   (c) digesting the PCR product with a restriction enzyme; and
   (d) analyzing the digested PCR product for nucleotide fragments of a first, second or third pattern; wherein the digested PCR product pattern determines the RhD zygosity of the subject.

2. The method of claim 1, wherein said first primer comprises SEQ ID NO:1 or a nucleotide sequence with at least 95% identity with SEQ ID NO:1.

3. The method of claim 1, wherein the nucleic acid is DNA.

4. The method of claim 1, wherein the restriction enzyme is PstI.

5. The method of claim 1, wherein the second primer has a nucleotide sequence with at least 95% identity to SEQ ID NO:3 or SEQ ID NO:2.

6. The method of claim 1, wherein the second primer has a nucleotide sequence with at least 99% identity to SEQ ID NO:3 or SEQ ID NO:2.

7. The method of claim 1, wherein the second primer has a nucleotide sequence comprising SEQ ID NO:3 or SEQ ID NO:2.

8. The method of claim 1, wherein the first primer hybridizes under stringent conditions to a nucleotide sequence in the region between positions 1 and 540 of SEQ ID NO:4, SEQ ID NO:5 or SEQ ID NO:6.

9. The method of claim 1 further comprising the step of sequencing the RhD gene to determine if the subject has a weak D allele, wherein a mutation within the RhD gene indicates the subject has a weak D allele.

10. The method of claim 1, wherein the first primer has a nucleotide sequence with at least 99% identity to SEQ ID NO:1, and wherein the primer is 21 to 30 nucleotides in length.

11. The method of claim 1, wherein the first primer comprises a nucleotide sequence of SEQ ID NO:1, and wherein the primer is 21 to 30 nucleotides in length.

* * * * *